United States Patent [19]

Rozzell

[11] Patent Number: 4,826,766

[45] Date of Patent: May 2, 1989

[54] PRODUCTION OF AMINO ACIDS USING COUPLED AMINOTRANSFERASES

[75] Inventor: J. David Rozzell, Cambridge, Mass.

[73] Assignee: Genetics Institute, Inc., Cambridge, Mass.

[21] Appl. No.: 779,157

[22] Filed: Sep. 23, 1985

[51] Int. Cl.$^4$ .................... C12P 13/22; C12P 13/12; C12P 13/08; C12P 13/06

[52] U.S. Cl. .................... 435/106; 435/108; 435/113; 435/115; 435/116; 435/191; 435/193; 435/176; 435/180

[58] Field of Search .............. 435/106, 107, 108, 109, 435/110, 113, 114, 115, 116, 41, 42, 191, 193, 176, 180, 188, 232

[56] References Cited

U.S. PATENT DOCUMENTS

| | | | |
|---|---|---|---|
| 3,183,170 | 5/1965 | Kitai et al. | 435/110 |
| 4,304,858 | 12/1981 | Wandrey et al. | 435/813 |
| 4,318,980 | 3/1982 | Boguslaski et al. | 435/810 |
| 4,416,992 | 11/1983 | Arena et al. | 435/180 |
| 4,446,231 | 5/1984 | Self | 435/810 |
| 4,518,692 | 5/1985 | Rozzell | 435/106 |
| 4,525,454 | 6/1985 | Rozzell | 435/106 |

FOREIGN PATENT DOCUMENTS 2152503  8/1985  United Kingdom .............. 435/108

OTHER PUBLICATIONS

Leuchtenberger et al, Enzyme Engineering #7, Annals of the N.Y. Acad. Sci. 434, pp. 78–86 (1984).

Kyowa, Japan, Kokai Tokkyo Koho 84:35,991, 08 Apr. 1981, pp. 1–5, Chem. Abst. 95:148701m.

*Primary Examiner*—John Edward Tarcza
*Attorney, Agent, or Firm*—David L. Berstein; Bruce M. Eisen

[57] ABSTRACT

This invention relates to a process for producing a desired alpha-amino acid, $AA_d$, or a derivative thereof. The process comprises:

(a) reacting a first alpha-amino acid, $AA_{NH2}$; a first alpha-keto acid, $KA_t$; a second alpha-keto acid, $KA_{pre}$; a first transaminase enzyme and a second transaminase enzyme to produce (i) the desired alpha-amino acid, $AA_d$ and (ii) a third alpha-keto acid, $KA_{prod}$; and (b) removing $KA_{prod}$ from the other keto acids, amino acids and enzymes wherein $AA_d$ and $KA_{pre}$, $AA_t$ and $KA_t$, and $AA_{NH2}$ and $KA_{prod}$ are interconvertible, respectively, by amino group transfer. The first transaminase efficiently catalyzes reaction (i), but not reaction (ii) and the second transaminase efficiently catalyzes reaction (ii) but not reaction (i):

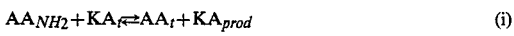

$$AA_{NH2} + KA_t \rightleftharpoons AA_t + KA_{prod} \qquad \text{(i)}$$

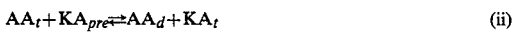

$$AA_t + KA_{pre} \rightleftharpoons AA_d + KA_t \qquad \text{(ii)}$$

In one embodiment $KA_{prod}$ is continuously removed from the reaction mixture thus driving the overall reaction to completion.

9 Claims, 2 Drawing Sheets

AMINO ACID ANALYSIS OF L-ALANINE
PRODUCT MIXTURE

CONDITIONS FOR L-ALANINE PRODUCTION (L-Aspartic Acid) = 0.42 M
(2-Ketoglutarate) = 0.017 M
(Pyridoxal Phosphate) = 0.16 mM
($MgCl_2$) = 8.2 mM pH = 6.5 - 8.0
Temperature : 23°C
Initial Rate : 3.6 mM/min.

PRODUCTION OF AMINO ACIDS USING COUPLED AMINOTRANSFERASES

This invention relates to a method for the production of amino acids by transamination of the corresponding 2-keto acids. Citations to various publications are provided throughout this application. The disclosures of these publications in their entireties are hereby incorporated by reference into this application in order to more fully describe the state of the art to which this invention pertains.

BACKGROUND OF THE INVENTION

Amino acids currently have application as additives to animal feed, nutritional supplements for human food, components in infusion solutions, and synthetic intermediates for the manufacture of pharmaceuticals and agricultural chemicals. L-glutamic acid is used as a flavor enhancer for food with a world market of over 1 billion dollars annually. L-lysine and methionine are large volume additives to animal feed, and L-tryptophan and L-threonine have similar potential applications. L-phenylalanine and L-aspartic acid have very important markets as key components in the manufacture of the sweetener aspartame. Infusion solutions require a range of amino acids including those essential in human diets.

Methods developed for the synethesis of amino acids involve fermentation, chemical synthesis, extraction from protein hydrolyzates, and enzymatic bioconversions. Chemical synthetic methods generally involve the initial formaation of a racemic mixture, followed by the resolution of this mixture to yield the optically active product. The resolution may be accomplished either chemically, by fractional crystallization of diasteromeric salts of the amino acid, or if desired, enzymatically using the enzyme L-aminocylase. The undesired isomer can be re-racemixed and then recycled through the process. Fermentation methods suffer from problems of slow rates of conversion, costly purifications, and very high capital investments. Extraction from protein hydrolyzates is used only in a few cases because the amino acid of interest is a relatively low percentage of the total protein. Enzymatic conversions offer advantages primarily due to reduced capital investments, lower purification costs, and higher rates of conversion.

One such previously described process involves the transamination of a given 2-ketoacid to the corresponding L-amino acid (U.S. Pat. No. 4,518,692 (May 1985)). In that process, L-aspartic acid and a 2-ketoacid are reacted in the presence of a transaminase to form the desired L-amino acid and oxaloacetate, followed by decarboxylation of said oxaloacetate to form pyruvate. The essentially irreversible decarboxylation of oxaloacetate drives the entire process to completion to form L-amino acids in yields approaching 100% of theoretical from the corresponding 2-ketoacids. The reaction is summarized in Scheme 1.

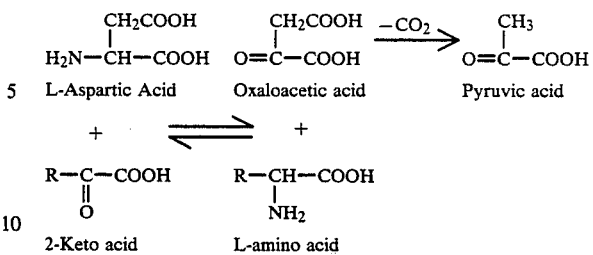

This process has the requirement that the transaminase employed in the practice of the invention accept L-aspartic acid as the amino group donor. There exist certain transaminases with desirable characteristics and specificities for use in biocatalytic processes, but which cannot use L-aspartic acid as the amino donor. The present invention is an improvement on the process of U.S. Pat. No. 4,518,692 described above; the present invention provides a method for achieving the advantages of using L-aspartic acid, as well as any of a variety of other amino acids, as the amino group donor in transamination reactions involving enzymes that utilize the amino acid so employed either poorly or not at all as an amino group donor.

SUMMARY OF THE INVENTION

This invention relates to a process for producing a desired alpha-amino acid, $AA_d$, or a derivative thereof. The process comprises:

(a) reacting a first alpha-amino acid, $AA_{NH2}$; a first alpha-keto acid, $KA_t$; a second alpha-keto acid, $KA_{pre}$; a first transaminase enzyme and a second transaminase enzyme to produce (i) the desired alpha-amino acid, $AA_d$ and (ii) a third alpha-keto acid, $KA_{prod}$; and (b) removing $KA_{prod}$ from the other keto acids, amino acids and enzymes wherein $AA_d$ and $KA_{pre}$, $AA_t$ and $KA_t$, and $AA_{NH2}$ and $KA_{prod}$ are interconvertible, respectively, by amino group transfer. The first transaminase efficiently catalyzes reaction (i), but not reaction (ii) and the second transaminase efficiently catalyzes reaction (ii) but not reaction (i):

$$AA_{NH2} + KA_t \rightleftharpoons AA_t + KA_{prod}$$

$$AA_t + KA_{pre} \rightleftharpoons AA_d + KA_t$$

In one embodiment $KA_{prod}$ is continuously removed from the reaction mixture thus driving the overall reaction to completion. Preferably, the amino and keto acids are selected such that recovery of $AA_d$ from starting materials may be conveniently effected by conventional methods. More specifically, $AA_{NH2}$ and $AA_t$ preferably have $pK_a$'s, solubilities, or other physicochemical properties sufficiently different from the corresponding properties of the desired amino acid, $AA_d$, such that recovery of $AA_d$ from any residual $AA_t$ or $AA_{NH2}$ may be readily accomplished in high yield.

DETAILED DESCRIPTION OF THE INVENTION

Figure 1:
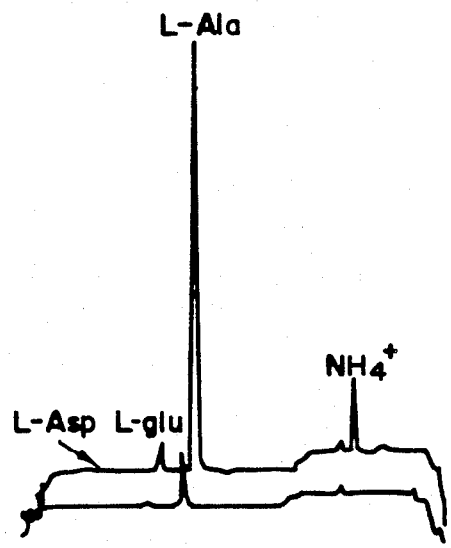
FIG. 1 depicts the amino acid analysis of an L-alanine product mixture.

This invention involves a process for producing a desired alpha-amino acid, $AA_d$, or a derivative thereof. The process involves reacting a first alpha-amino acid, $AA_{NH2}$, (the ultimate amino donor); a first alpha-keto acid, $KA_t$, a second alpha-keto acid, $KA_{pre}$ (the ultimate amino acceptor); and two transaminase enzymes to produce the desired alpha-amino acid, $AA_d$, and as a by-product, a third alphaketo acid, $KA_{prod}$. As discussed in greater detail below, the process also requires removal of $KA_{prod}$ from the reaction system, i.e., from the other keto acids, amino acids and enzymes. $KA_{pre}$, $KA_t$, $AA_{NH2}$ and the two transaminases are selected in each embodiment of this invention such that the following transamination conversions obtain:

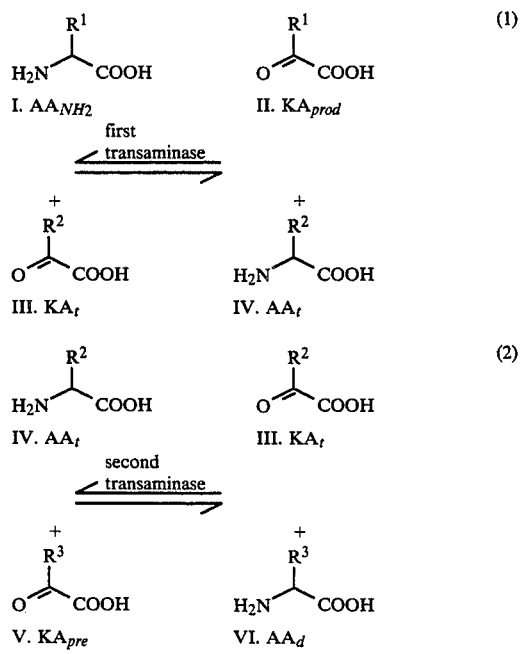

As indicated in reactions (1) and (2) above, $AA_{NH2}$ and $KA_{prod}$, $AA_t$ and $KA_t$, and $AA_d$ and $KA_{pre}$ are interconvertible, respectively, by amino group transfer.

In view of the preceding it should be clear that in comparison to prior transamination methods for producing amino acids, see e.g. U.S. Pat. No. 4,518,692, the method of the subject invention requires the use of an additional keto acid ($KA_t$) and transaminase enzyme. The subject method more than compensates for these additional requirements in that it overcomes the twofold substrate specificity of transaminase enzymes, i.e. the specificity with respect to both the amino group donor and acceptor. The substrate specifities of transaminase enzymes have heretofore been a major limitation on their use in the production of amino acids. For example, certain transaminases with otherwise desirable characteristics and specificity are known which cannot use L-aspartic acid as the amino group donor. Such transaminases are therefore not suitable for use in the method of U.S. Pat. No. 4,518,692. In contrast to prior methods, the subject method permits transamination of a keto acid, $KA_{pre}$, to form the desired amino acid, $AA_d$, using a transaminase enzyme of the necessary specificity and selectivity to catalyze the transamination of $KA_{pre}$ but not capable of efficiently utilizing a conveniently available, inexpensive or otherwise preferred amino acid as the amino group donor for the transamination. This objective is accomplished in the subject invention by using a first transaminase enzyme capable of using a pre-selected amino acid as an amino group donor, although lacking the substrate specificity for the intended amino group acceptor, i.e. $KA_{pre}$, in the presence of a second transaminase enzyme capable of transaminating $KA_{pre}$ using as the amino group donor the amino acid which is the transamination product of the first transaminase. To summarize the specificities of the two transaminases with respect to reactions (1) and (2) above, the first transaminase must be capable of efficiently catalyzing reaction (1) but not reaction (2), while the second transaminase must be capable of efficiently catalyzing reaction (2) but not reaction (1). By "efficiently catalyzing" one reaction but not another, as the term is used herein, is meant catalyzing one reaction with a rate constant at least about ten-fold greater than for the other reaction. For example, the rate constant of the first transaminase for reaction (1) should be at least about ten times the rate constant of that enzyme for reaction (2). Mechanistically, this relationship results from the fact that the first transaminase is capable of using $AA_{NH2}$ as an amino group donor but not of using $KA_{pre}$ as an amino group acceptor while the second transaminase is capable of using $KA_{pre}$ as an amino group acceptor but not of using $AA_{NH2}$ as an amino group donor.

In the course of the reactions depicted above the amino group of $AA_{NH2}$ is transferred to $KA_t$ to generate $AA_t$ from which in turn an amino group is transferred to $KA_{pre}$ to yield the desired alpha-amino acid, $AA_d$. Thus by choosing the appropriate keto acid precursor, $KA_{pre}$, the desired alpha-amino acid, $AA_d$, may be produced.

The coupled nature of these reactions is depicted schematically below:

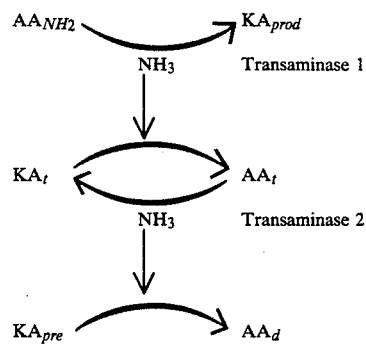

As shown in the reaction scheme above, the transamination of $KA_{pre}$ to yield $AA_d$ also regenerates $KA_t$. The cyclic inter-conversion of $KA_t$ and $AA_t$ thus serves to transfer an amino group from the ultimate amino group donor, $AA_{NH2}$, to the ultimate amino group acceptor, $KA_{pre}$. This transfer function is reflected in the "t" subscript in the terms "$AA_t$" and "$KA_t$". In view of the cyclic interconversion of $KA_t$ and $AA_t$, as illustrated above, it should be understood that $KA_t$ may be indirectly added to the reaction mixture by reacting $AA_{NH2}$, $AA_t$ and $KA_{pre}$ in the presence of the two transaminases. Such "indirect" supplying of $KA_t$ via the corresponding amino acid, $AA_t$, is preferred in cases wherein the amino acid is less expensive or more readily available than the corresponding keto acid. It should be noted that another 2-keto acid, $KA_{prod}$, is produced as a by-product of the coupled reactions along with $AA_d$.

By choosing appropriate transaminase enzymes, either D- or L-amino acids may be specifically produced by the method of this invention. For example, where D-amino acids are desired, one would typically utilize D-transaminases, which are specific for D-amino acids. A number of D-transaminases have been isolated which will catalyze the synthesis of D-amino acids. See *Biochemical and Biophysical Research Communications*, 122:485–491 (1984); Yonaha, K., et al, *Amino Acid, Nucl. Acid* (Japan), 32:34–35 (1975); Soper, T. S., and Manning, J. M., *J. Biol. Chem.*, 256:4263–4268 (1981); and Soper, T. S., et al, *J. Biol. Chem.*, 252:1571–1575 (1978) which are incorporated herein by reference. These and any other transaminases which will result in the formation of a D-amino acid can readily be utilized in the process described herein.

The advantages of this coupled transamination technology are:

1. The desired optically pure D- or L-amino acids are produced specifically. The undesired optical isomer is not produced and no optical resolution is required.

2. The 2-keto acid precursors are conveniently available from chemical synthesis or may be produced in situ from conveniently available corresponding amino acids.

3. The rates of reaction are relatively rapid.

4. The capital costs are lower than for a fermentation process.

5. The technology is general because transaminases with varying selectivities are known, e.g. aromatic amino acid transaminases, branched chain amino acid transaminases, transaminases specific for amino acids having acidic side chains, etc. Such transaminases can be prepared, for example, from the following microorganisms; *Escherichia coli (E. coli), Bacillus subtilis, Bacillus stearothermophilus, Achromobacter eurydice, Klebsiella aerogenes, Saccharomyces cerevisiae, Pseudomonas putida*, and the like. Some transaminases useful in the practice of this invention are also described by H. E. Umbarger in Annual Rev. Biochem., Vol. 47, pp. 533–606 (1978) and in Amino Acids: Biosynthesis and Genetic Regulation, K. M. Herrmann and R. L. Somerville, eds., pp. 19-34 (Addison-Wesley, 1983). Some other useful transaminases are listed in Enzyme Nomenclature, pp. 220-230 (Academic Press, 1984).

6. A desired amino acid can be produced using a corresponding keto acid, a conveniently available amino donor and an appropriate transaminase, even though the transaminase enzyme can use the amino donor poorly or not at all.

The single greatest disadvantage of such enzymatic methods is that the equilibrium constants for each transamination reaction as written will be about 1.0. As a result, the yield of the desired amino acid, $AA_d$, for the reaction as written above will never exceed about 50% based on the amount of $AA_{NH2}$ used.

The problem of incomplete conversion is solved in the present invention by removing $KA_{prod}$ as it is formed, from the other keto-acids, amino acids and enzymes. By way of example, $KA_{prod}$ may be continuously reduced enzymatically, e.g. by the methods disclosed in MakryaleasKyriakos et al., Chem. Ing. Tech. 57:362–363 (1985); Wandrey-Christian et al. European Patent Application No. 040281 (1981); Buckman et al., U.S. Pat. No. 4,304,858 (1985), etc. Alternatively, $KA_{prod}$ may be continuously reduced in the in the presence of a multi-enzyme system, hydrogen gas, and a nitrogen source, such as ammonium salt, organic ammonium salt, ammonium hydroxide, ammonia gas, or urea. See U.S. Pat. No. 3,183,170. By such methods $KA_{prod}$ is removed from the reaction system in the sense that it is converted to $AA_{NH2}$. Alternatively, $KA_{prod}$ may be continuously reduced as it is formed to yield the corresponding alpha-hydroxcarboxylic acid, e.g. by the method of Buckman et al., U.S. Pat. No. 4,326,031 (1985). Preferably, however, in embodiments wherein $KA_{prod}$ is a 2-keto carboxylic acid, $KA_{prod}$ is removed from the reaction system by a decarboxylation reaction which is essentially irreversible under typical reaction conditions. For example, where $AA_{NH2}$ is L-aspartic acid, $KA_{prod}$, i.e. oxaloacetate, is decarboxylated, essentially irreversibly, to pyruvic acid.

When alanine is used as the amino donor, $AA_{NH2}$, the 2-keto acid byproduct, pyruvate, may be decarboxylated to acetaldehyde. This reaction may be catalyzed by compounds such as cyanide, thiamine, or thiamine pyrophosphate, or more preferably, by the enzyme pyruvate decarboxylase (E.C. 4.1.1.1). Utter, M. F., *The Enzymes*, 5:320 (1981).

Similarly, if glutamic acid is used as the amino group donor, $AA_{NH2}$, the byproduct 2-ketoglutarate can be decarboxylated to succinic semialdehyde. Again this reaction can be catalyzed chemically or enzymatically. An enzyme is available from wheat germ (named pyruvate decarboxylase) (E.C. 4.1.1.1) which decarboxylates 2-ketoglutarate in addition to pyruvate. Sincer, T. R. and Pensky, J., *J. Biol. Chem.*, 196:375 (1952).

By coupling such an essentially irreversible removal of $KA_{prod}$ to the coupled transamination reactions, the net transamination of $KA_{pre}$ is driven to completion as depicted below:

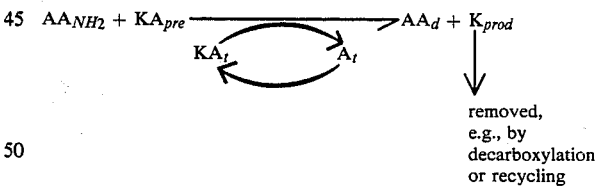

removed, e.g., by decarboxylation or recycling

Decarboxylation of $KA_{prod}$ may be effected by methods which are known in the art. For example, in the embodiment wherein $AA_{NH2}$ is aspartic acid the decarboxylation of oxaloacetate can be catalyzed either thermally; chemically by various metal ions, amines, and/or acids; or preferably enzymatically, e.g. by the enzyme oxaloacetate decarboxylase (OAD) E.C. 4.1.1.3 as well as by any combination of these methods. Oxaloacetate decarboxylase from any source can be used. Examples of sources of oxaloacetate decarboxylase useful in the practice of the present invention are, for instance, *Micrococcus luteus*, renamed from *Micrococcus lysodeikticus* (see Methods in Enzymology 1-753-7 (1955) which is incorporated by reference. *Pseudomonas putida* (see Biochem. Biophys. Acta 89, 381-3 (1964) which is hereby incorporated by reference), and *Azotobacter*

*vinelandii* (see J. Biol. Chem. 180, 13 (1949) which is hereby incorporated rated by reference), etc. Also, any other enzyme having a oxaloacetate decarboxylase activity but not usually regarded as an "oxaloacetate decarboxylase" may be used such as, for instance, pyruvate kinase, malic enzyme, etc. The activity of oxaloacetate decarboxylase can be enhanced by adding metal ions such as, for example, $Mn^{++}$, $Cd^{++}$, $Co^{++}$, $Mg^{++}$, $Ni^{++}$, $Zn^{++}$, $Fe^{++}$, $Ca^{++}$ and the like.

One limitation on the choice of a particular enzymatic or other method for removing $KA_{prod}$ is that the method must not interfere with the conversion of $KA_t \rightleftarrows AA_t$ or $KA_{pre} \rightarrow AA_d$ or the accumulation of $AA_d$. Thus, in the embodiment wherein $AA_{NH2}$ is L-aspartic acid, the decarboxylase enzyme must be sufficiently specific for oxaloacetate so as to not decarboxylate $KA_t$ or $KA_{pre}$ to any appreciable extent.

In one embodiment the decarboxylation of $KA_{prod}$ produces $KA_{pre}$ in situ, as illustrated schematically below:

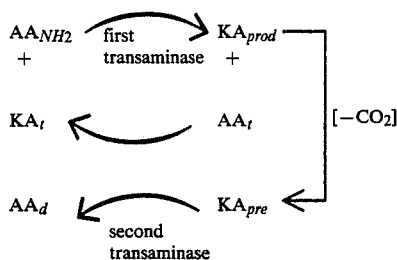

For example, in the production of alanine using aspartic acid as the amino donor ($AA_{NH2}$), $KA_{prod}$ (oxaloacetate) is decarboxylated to produce pyruvate which is also the $KA_{pre}$ corresponding to the desired amino acid alanine:

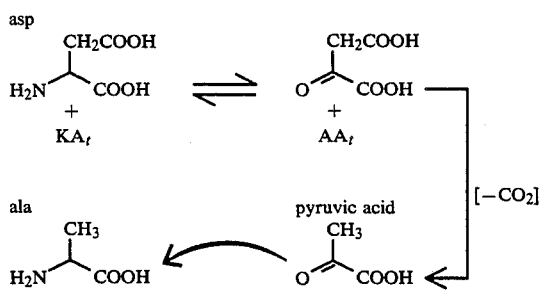

Numerous other examples will be recognized by one skilled in this art having the benefit of this disclosure in which a desired amino acid may be produced by transamination of a $KA_{pre}$ derived from the ultimate amino donor, $AA_{NH2}$. In these examples $KA_{pre}$ is provided indirectly by decarboxylation of $KA_{prod}$ and therefore need not be independently added to the reaction mixture. Thus, in the example depicted above $KA_{pre}$, i.e. pyruvic acid, is produced in situ and need not be separately added to the reaction mixture.

The process of this invention can thus be used for the production and recovery of a large variety of D- or L-amino acids by choosing the proper 2-keto acid precursor and enzyme capable of transaminating it with $AA_t$ but not with $AA_{NH2}$. The process is equally applicable to the production of amino acids containing one or more stable or radioactive isotopes such as $^{14}C$, $^{13}C$, $^2H$, $^3H$, $^{17}O$, $^{18}O$, or $^{15}N$ simply by using an appropriately isotopically labeled $KA_{pre}$, $AA_{NH2}$, or water solvent.

As a further example of this invention, the amino acid L-valine may be prepared in high yield from 2-ketoisopentatonic acid, L-glutamic acid and L-aspartic acid using a branched-chain transaminase isolated from *E. coli*, asparate transaminase also isolated from *E. coli* and an oxaloacetate decarboxylase isolated from either *Pseudomanas putida, A z o tobacter vinelandii*, or *Micrococcus luteus*. Similarly, using these same enzymes, 2-ketoisocaproic acid may be converted into L-leucine and 2-keto-3-methylpentanoic acid into L-isoleucine. By using transaminases with different specificities, phenyl pyruvic acid may be transaminated to L-phenyl alanine, 3-hydroxypyruvate to L-serine, 3-indoylpyruvate to L-tryptophan, 2-ketoadipic acid to L-2-aminoadipic acid, 2-keto-3-mercaptopropionic acid to L-cysteine, glyoxylic acid to glycine, and 2-oxo-4-thiomethylbutanoic acid to L-methionine.

The R groups in the amino acids, $AA_{NH2}$, $AA_t$, and $AA_d$, and in the corresponding keto acids, $KA_{prod}$, $KA_t$ and $KA_{pre}$, can be selected from a wide variety of substituents including, for example hydrogen, substituted and unsubstituted lower alkyl, substituted and unsubstituted lower aryl, and heterocyclic groups.

The term "lower alkyl" as used herein means both straight chain and branched chain alkyl groups having from one to about 10 carbon atoms. "Substituted lower alkyl" groups means lower alkyl groups substituted at any location with hydroxy, alkoxy, mercapto, carbamoyl, fluoro, chloro, bromo, iodo, amino, amidino, and R'-thio (where R' is lower alkyl or substituted lower alkyl or lower aryl or substituted lower aryl) groups. These groups include those found in natural amino acids as well as unnaturally occurring amino acids.

The term "lower aryl" as used herein means phenyl, benzyl, phenylethyl, phenylpropyl, and other homologous groups. "Substituted lower aryl" groups include phenyl, benzyl, phenylethyl, phenylpropyl, and other homologous groups substituted with the same groups as those listed above for lower arkyl.

Heterocyclic groups as used herein means 4-imidazoylmethyl, 3-indoylmethyl, homologous groups to these, and other similar heterocyclic groups.

In some cases the byproduct of the removal of $KA_{prod}$ is a valuable commercial product and can be recovered from the product stream by any method described in the prior art, such as acidification and distillation, ion exchange, solvent extraction and the like. Such is the case where $KA_{prod}$ is oxaloacetate, in which case decarboxylation yields pyruvic acid.

The enzymatic reactions of this invention may be carried out at temperatures ranging from about 4° C. to about 80° C., most preferably from about 20° C. to about 65° C. The optimal pH for the reactions ranges from about 2.0 to about 12.0, most preferably from about 4.0 to about 9.5. The small molecule pyridoxal phosphate is preferably used as a cofactor for the transaminase enzymes, and may be added at a concentration of about 0.01 millimolar to about 1.0 millimolar.

The enzymes used in this invention can be added to the reaction mixture in whole cells, crude cell lysates, as partially purified enzyme or purified enzyme. Preferably purified or partially purified enzymes are used, either immobilized or in solution, because the conversion rates per unit weight of enzyme are higher. The enzymes can be purified by techniques well known to those skilled in the art. Examples of purification of oxaloacetate decarboxylase from *Micrococcus luteus* and *Pseudomonas putida* are described by Herbert, Methods in Enzymology 1, pp. 753–57 (1955) and by Morton et al., Biochem. Biophys. Acta. 89, pp. 381–83 (1964).

The enzymes can be used in solution or as immobilized enzymes, as aforesaid, in the practice of this invention.

Immobilization methods which may be used in the practice of this invention include entrapment in polymeric gels, covalent attachment, crosslinking, adsorption and encapsulation as described, e.g., by A. M. Klibanov, Science 219: 722–727 (1983) and references therein and in Methods in Enzymology 44 (K. Mosbach, ed.). One example of an immobilized enzyme system is described by Weetall et al., Methods in Enzymology 34, pp. 59–72 (1974), which is hereby incorporated by reference. Weetall et al. describe a method for immobilizing enzymes on glutaraldehyde activated controlled pore glass beads (Corning).

In accord with this method, transaminases may be coupled to the glass particles by reacting the enzymes with the activated glass particles at 0°–5° C. for 2 hours in a phosphate buffer solution having a pH of 7.0. The coupled enzymes can be used directly or first reacted with 1% sodium borohydride to stabilize the covalent link between the enzyme and the activated glass.

In another embodiment, alumina or silica particles are first impregnated with polyethyleneimine, followed by activation with glutaraldehyde. The enzyme is then covalently attached to the activated support.

Other suitable sustrates for immobilizing enzymes for the practice of this invention include porous ceramic, porous silica, bentonite, diatomaceous earth, sepharose, cellulose and ellulose derivates, polyacrylamide, polyazetidine, carrageenan, chromosorb, and the like. These substances can be activated, if desired, by techniques well known in the art.

Enzymes used to remove $KA_{prod}$ from the reaction system may be similarly treated. By way of example, the oxaloacetate decarboxylase is either immobilized separately, or first mixed with the transaminases and the mixture coimmobilized. Porous silica particles on which the enzymes had been covalently attached by the aforedescribed procedures were suspended in a solution containing 100 mM 2-ketoisovalerate, 100 mM L-aspartic acid, 20 mM L-glutamic acid, 0.1 mM pyridoxal phosphate, 10 mM $MgCl_2$ or $MnSO_4$, pH adjusted to the range 4.0–10.0 and most preferably between 5.5 and 8.5. When all the phenylpyruvate had been consumed, the solution was filtered away from the immobilized enzymes and the products valine and pyruvic acid isolated and purified by conventional methods.

The reaction may also be carried out in continuous flow mode by packing the immobilized enzymes into a bioreactor. Numerous configurations for such bioreactors are known in the art. For example, two (2) grams of porous silica (Corning) containing the immobilized *E. coli* aspartic and branched chain transaminases was poured into a 1×10 cm column and a solution containing 2-ketoisovalerate (100 mM), L-aspartic acid (100 mM), L-glutamic acid (20 mM), and pyridoxal phosphate (0.1 mM) was pumped through the column using a conventional peristaltic pump. Analysis of the effluent of the column showed L-valine and pyruvate as the reaction products.

The production of L-amino acids can be monitored if desired. For example, a general assay which is applicable to the assay of all transamination reactions using L-aspartic acid as the amino donor regardless of the 2-keto acid precursor that is used is the following: L-aspartic acid, a 2-keto acid, transaminase, NADH, and the enzyme malic dehydrogenase (available commercially) are dissolved in solution of phosphate buffer at a pH between 6.0 and 9.0; the change in the absorbance at 340 nm ($A_{340}$) with time is measured. This change in the absorbance at 340 nm corresponds to the consumption of NADH during the reduction of oxaloacetate, formed from L-asparate during the transamination reaction.

As an alternative, for instance, the conversion of phenylpyruvate to L-phenylalanine can be conveniently assayed by taking aliquots from the reaction mixture containing, for instance, transaminase, phenylpyruvate, L-asparate, oxaloacetate decarboxylase, and metal ions, diluting them into a solution 2.5% sodium hydroxide in water (w/v), and measuring the absorbance at 320 nm. Dilution into sodium hydroxide causes rapid achievement of the equilibrium between the keto and enol forms of phenylpyruvate. The extinction coefficient at 320 nm for the equilibrium mixture is 17,500 $M^{-1} cm^{-1}$. Thus, the conversion of phenylpyruvate into L-phenylalanine can be quantitated rapidly. This assay can be corroborated by measuring L-phenylalanine qualitatively by paper chromatography and quantitatively using an amino acid analyzer.

Similar techniques can be used to assay for the conversion of other 2-keto acids into the corresponding D- or L-amino acids. The transamination of p-hydroxyphenylpyruvate to L-tyrosine can be monitored by diluting aliquots removed from the reaction mixture into 2.5% NaOH and measuring the absorbance at 331 nm (extinction coefficient of 19,900 $M^{-1} cm^{-1}$, and the conversion of indole-3-pyruvate into L-tryptophan can likewise be followed by measuring the absorbance at 328 nm (extinction coefficient of 10,000 $M^{-1} cm^{-1}$).

The invention will now be further illustrated by the following examples which are given here for illustrative purposes only and are not intended to, and should not be construed to, limit the scope of the invention.

EXAMPLES

EXAMPLE 1

PREPARATION OF L-ALANINE

Five milliliters of a solution containing L-aspartic acid (20 mM), 2-ketoglutarate (5 mM), Glutamic-oxaloacetic transaminase from porcine heart purchased from Lee Scientific, St. Louis, Missouri, (100 units), oxaloacetic decarboxylase isolated from *Pseudomonas putida* ATCC 950 (100 units), glutamic-pyruvic transaminase purchased from Lee Scientific (50 units), $MgCl_2$ (10 mM), pyridoxal phosphate (0.2 mM), sodium borate (10 mM) were incubated at 25° C. for 12 hours in a rotary shaker. At the end of this time, the reaction was analyzed for all amino acids by amino acid analysis (Beckman Model 6300). The product mixture contained 18.9 mM L-alanine and 1.1 mM L-glutamic acid as the only amino acids present as illustrated in FIG. 1. There was no detectable L-aspartic acid. The molar yield of L-alanine from L-aspartic acid was 95%.

EXAMPLE 2

PRODUCTION OF L-ALANINE

Figure 2:
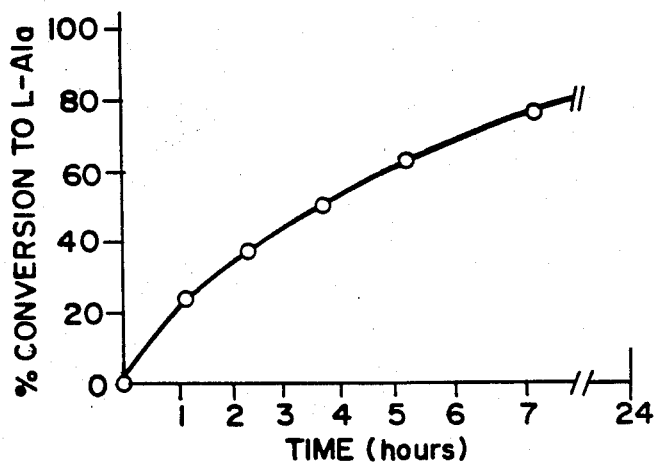
FIG. 2 depicts the reaction progress for the production reaction conditions comprising a pH of 6.5–8.0, a temperature of 23° C., an initial rate of 3.6 mH/min, and the following concentrations: 0.42 M L-Aspartic Acid, 0.017 M 2- Ketoglutarate, 0.16 mM Pyridoxal phosphate and 8.2 mM MgCl$_2$ of L-alanine from L-aspartic acid under.

The enzymatic reaction was carried out exactly as in Example 1 except that the concentration of L-aspartic acid was 420 mM and the concentration of 2-ketoglutarate was 17 mM. Assay of the product by amino acid analysis again showed complete conversion of the L-aspartic acid to produce L-alanine and L-glutamic acid. The reaction progress of this example repeated under similar conditions but with a reaction time of 24 hrs. is illustrated graphically in FIG. 2.

EXAMPLE 3

ALTERNATIVE PRODUCTION OF L-ALANINE

A five milliliter solution containing L-aspartic acid (100 mM), 2-ketoglutarate (5 mM), pyridoxal phosphate (0.4 mM), $MgCl_2$ (10 mM), GOT (4.2 units; Lee Scientific), GPT (4.2 units; Lee Scientific); OAD (4.2 units; *P. Putida*), sodium borate (50 mM), initial pH=7.0. Incubation was for 12 hrs. at 24° C. Amino acid analysis carried out as before showed complete conversion of the L-aspartic acid. L-alanine and L-glutamic acid were the only amino acids present in relative concentration of 95.6 mM to 4.4 mM respectively.

EXAMPLE 4

PRODUCTION OF L-ALANINE USING IMMOBILIZED ENZYMES

Glutamic-oxaloacetic transaminase (GOT; Lee Scientific) was immobilized on controlled pore glass (Pierce) that had been activated with triethoxy-3-aminopropyl silane as described by Weetall. A sample set of immobilization are given: 1.0 g aminopropyl glass; 100 mg lyophilized GOT, 18.2 units/mg; 100 mg ethyl dimethylaminopropyl carbodiimide; 20 mM 2-ketoglutarate; 0.5 mM pyridoxal phosphate; 10 mM sodium borate; pH 7.2. The mixture was agitated at 4° C. overnight. Glutamic-pyruvic transaminase (GPT; Lee Scientific), 4.9 units/mg protein, was immobilized in an identical manner. Oxaloacetate decarboxylase (*P. Putida*) was immobilized on CNBr-activated Sepharose (Pharmacia) in the presence of 10 mM $MgCl_2$ in 10 mM sodium borate, pH 8.0. A solution containing L-aspartic acid (100 mM), 2-ketoglutarate (5 mM), $MgCl_2$ (10 mM), Sodium borate (20 mM), pyridoxal phosphate (0.4 mM) having a pH of 7.2 was circulated at a flow rate of 0.5 ml/min. through three small columns each containing 1.0 g of GOT, OAD, or GPT immobilized enzyme preparations. Yield of L-alanine was determined by amino acid analysis of the fractions to be 94% from L-aspartic acid.

EXAMPLE 5

IMMOBILIZATION OF BRANCHED-CHAIN TRANSAMINASES FROM *E. COLI*

One hundred mg of *E. coli* branched-chain transaminase was disolved in 50 ml of 50 mM potassium phosphate buffer (pH 7.0) containing pyridoxal phosphate (0.2 mM). Aminopropyl silica (2.0 g, prepared as described by Weetall) was added, followed by ethyldimethylaminopropyl carbodiimide hydrochloride (100 mg). The reaction was allowed to proceed for 1 hr. at 22° C. The silica was then washed with 200 ml of 200 mM potassium phosphate buffer, (pH 7.0) containing 0.5 m NaCl, followed by 200 ml of 50 mM potassium phospahte containing 0.2 mM pyridoxal phosphate (pH 7.0). The immobilized enzyme was stored at room temperature for subsequent use.

EXAMPLE 6

PRODUCTION OF L-VALINE

Figure 3:
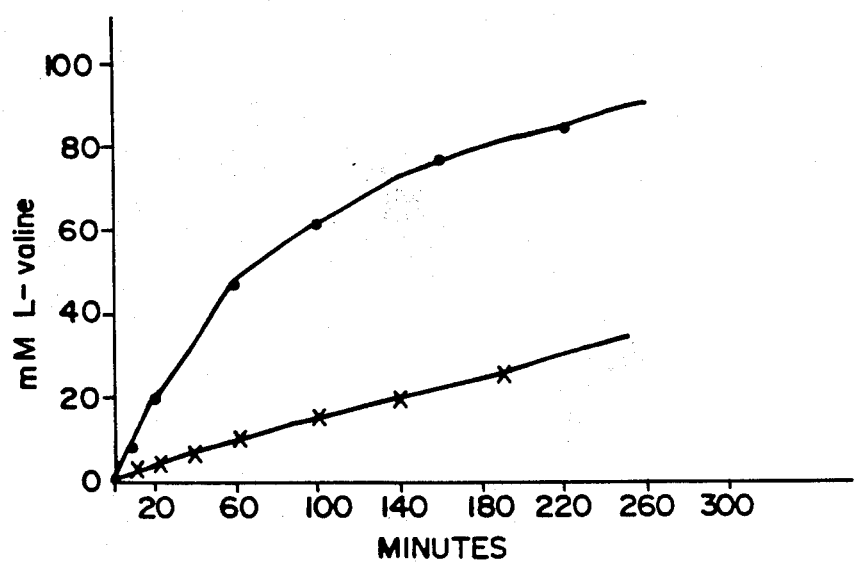
FIG. 3 depicts a comparison of the production of L-valine using coupled transamination in the presence and absence of decarboxylation.

In order to demonstrate the effect of the driving of the reaction to completion by decarboxylation of $KA_{prod}$, two identical reactions were carried out differing only in that the enzyme oxaloacetate decarboxylase was added to one reaction mixture, but not the other. In one case, a five milliliter solution containing L-aspartic acid (100 mM), L-glutamic acid (20 mM), 2-ketoisopentanoic acid (100 mM), pyridoxal phosphate (0.2 mM0, magnesium chloride (10 mM), asparate transaminase from *E. coli* (50 units), branched-chain transaminase from *E. coli* (5 units), oxaloacetate decarboxylase from *Pseudomonas putida* (50 units), pH 7.5 was prepared. An identical reaction mixture without the oxaloacetate decarboxylase was prepared in parallel. Both reactions were carried out at 25° C. The reactions were monitored by quantitating the amount of oxaloacetate and pyruvate produced in each case. Quantification was effected by enzymatic methods as described in Methods of Enzymatic Analysis. The results of this experiment are presented graphically in FIG. 3. As illustrated by these results, decarboxylation of $KA_{prod}$ produces a significant shift in the concentration of the desired product, here, L-valine, effecting an almost five-fold increase in valine concentration at 1 hr., for example.

EXAMPLE 7

PRODUCTION OF L-LEUCINE

A 10 milliliter solution containing L-aspartic acid (100 mM), L-glutamic acid (20 mM), 2-ketoisocaproic acid (100 mM), pyridoxal phosphate (0.2 mM), magnesium chloride (10 MM), aspartate transaminase from *E. coli* (50 units), branched-chain transaminase from *E. coli* (5 units), oxaloacetate decarboxylase from *Pseudomonas putida* (50 units), pH 7.5 adjusted with sodium hydroxide was incubated at 25° C. for 3 hours. At the end of this time the reaction mixture was analyzed for total oxaloacetate and pyruvate as described above and also by amino acid analysis. The yield of L-leucine from 2-keotisocaproate was 85%.

EXAMPLE 8

PRODUCTION OF ISOLEUCINE

A 10 milliliter solution containing L-aspartic acid (100 mM), L-glutamic acid (20 mM), 2-keto-3-methylpentanoic acid (100 mM), pyridoxal phosphate (0.2 mM), magnesium chloride (10 mM), aspartate transaminase from *E. coli* (50 units), branched-chain transamainase from *E. coli* (5 units), oxaloacetate decarboxylase from *Pseudomonas putida* (50 units), pH 7.5 adjusted with sodium hydroxide was incubated at 25° C. for 3 hours. At the end of this time the reaction mixture was analyzed for total oxaloacetate and pyruvate as described earlier. The yield of L-isoleucine from the 2-ketoacid was 88%.

EXAMPLE 9

PRODUCTION OF L-CYSTEINE

L-cysteine may be produced as follows:
A milliliter solution containing L-aspartic acid (100 mM), L-glutamic acid (20 mM), 3-mercaptopyruvate (100 mM), pyridoxal phosphate (0.2 mM), magnesium chloride (10 mM), aspartic glutamic aminotransferase (E.C. 2.6.1.1, 50 units) cysteine aminotransaminase (E.C. 2.6.1.3) (5 units), oxaloacetate decarboxylase from *Pseudomonas putida* (50 units)), pH 7.5 adjusted with sodium hydroxide is incubated at 25° C. for 3 hours. At the end of this time the reaction mixture may be analyzed for total oxaloacetate and pyruvate as described above and also by amino acid analysis.

EXAMPLE 10

PRODUCTION OF L-TRYPTOPHAN

L-tryptophan may be produced by repeating the method of Example 9 substituting 3-indoylpyruvate and tryptophan aminotransferase (E.C. 2.6.1.27) for 3-mercaptopyruvate and cysteine aminotransferase, respectively.

EXAMPLE 11

PRODUCTION OF L-PHENYLALANINE

L-phenylalanine may be produced by repeating the method of Example 9 substituting phenylpyruvate and aromatic aminotransferase (E.C. 2.6.1.57) for 3-mercaptopyruvate and cysteine aminotransferase, respectively.

EXAMPLE 12

ALTERNATIVE PRODUCTION OF L-VALINE

L-Valine may be produced as follows:

A 10 milliliter solution containing L-alanine (100 mM), L-glutamic acid (20 mM), 2-ketoisocaproic acid (100 mM), pyridoxal phosphate (0.2 mM), magnesium chloride (10 mM), glutamic pyruvic transaminase (E.C. 2.6.12, 5 units) branched-chain transaminase (E.C. 2.6.1.42, 5 units) pyruvate decarboxylase (E.C. 4.1.1.1 50 units), pH 7.5 adjusted with sodium hydroxide is incubated at 25° C. for 3 hours. At the end of this time the reaction mixture may be analyzed for total 2-ketoglutarate and pyruvate as described above and also by amino acid analysis.

EXAMPLE 13

ALTERNATIVE PRODUCTION OF L-PHENYLALANINE

L-Phenylalanine may be produced as follows:

A 10 milliliter solution containing L-glutamic acid (100 mM), L-alanine (20 mM), 2-keto-3-methylpentanoic acid (100 mM), pyridoxal phosphate (0.2 mM), magnesium chloride (10 mM), glutamic pyruvic transmainase (E.C. 2.6.1.2, 50 units), phenylalanine-pyruvate aminotransferase (E.C. 2.6.1.58, 5 units) pH 7.5 adjusted with sodium hydroxide is incubated at 25° C. for 3 hours. At the end of this time the reaction mixture may be analyzed for total oxaloacetate and pyruvate as described earlier.

EXAMPLE 14

PRODUCTION OF D-METHIONINE

D-Methionine may be produced as follows:

A 10 milliliter solution containing D-glutamic acid (100 mM), D-alanine (20 MM), 4-thiomethyl-2-ketobutanoate (100 mM), pyridoxal phosphate (0.2 mM), magnesium chloride (10 mM), D-alanine aminotransferase (E.C. 2.6.1.21, 50 units), D-Methionine-pyruvate aminotransferase (E.C. 2.6.1.41, 5 units), pH 7.5 adjusted with sodium hydroxide is incubated at 25° C. for 3 hours. At the end of this time the reaction mixture may be analyzed for total 2-ketoglutarate and pyruvate as described above and also by amino acid analysis.

EXAMPLE 15

PRODUCTION OF TAURINE

Taurine may be produced as follows:

A 10 milliliter solution containing L-asparatic acid (100 mM), L-glutamic acid (20 mM), sulfoacetaldehyde (100 mM), phyridoxal phosphate (0.2 mM), magnesium chloride (10 mM), aspartic glutamic aminotransferase (E.C. 2.6.1.1, 50 units), taurine aminotransferase (E.C. 2.6.1.55, 5 units) oxaloacetate decarboxylase from *Pseudomonas putida* (50 units) pH 7.5 adjusted with sodium hydroxide is incubated at 25° C. for 3 hours. At the end of this time the reaction mixture may be analyzed for total oxaloacetate and pyruvate as described earlier.

EXAMPLE 16

ALTERNATIVE PRODUCTION OF L-PHENYLALANINE

L-Phenylalanine may be produced from L-alanine as follows.

A 10 milliliter solution containing L-alanine (100 mM, L-glutamine (20 mM), phenylpruvate (100 mM), pyridoxal phosphate (0.2 mM0, magnesium chloride (10 mM), glutaminepyruvate transaminase (E.C. 2.6.1.5,50 units), glutaminephenylpyruvate transaminase (E.C. 2.6.1.64, 5 units) pyruvate decarboxylase E.C. 4.1.1.1 (50 units), pH 7.5 adjusted with sodium hydroxide is incubated at 25° C. for 3 hours. At the end of this time the reaction mixture may be analyzed for total 2-ketoglutamate and pyruvate as described earlier.

EXAMPLE 17

PRODUCTION OF 5-AMINOLEVULINATE

5-Aminolevulinate may be produced as follows:

A 10 milliliter solution containing L-alanine (20 mM), L-glutamic acid (100 mM), 4.5 diketopentanoate (100 mM), pyridoxal phosphate (0.2 mM), magnesium chloride (10 mM), glutamic pyruvic transaminase (E.C. 2.6.1.2, 5 units), aminolevulinate transaminase (E.C. 2.6.1.43, 50 units), pyruvate decarboxylase (E.C. 4.1.1.1., 50 units), pH 7.5 adjusted with sodium hydroxide is incubated at 25° C. for 3 hours. At the end of this time the reaction mixture may be analyzed for total 2-ketoglutarate and pyruvate as described above and also by amino acid analysis.

What is claimed is:

1. A process for producing a desired alpha-amino acid, $AA_d$, or a derivative thereof, which process comprises:
   (a) reacting a first alpha-amino acid, $AA_{NH2}$; a first alpha-keto acid, $KA_t$; and, a second alpha-keto acid, $KA_{pre}$; in a bioreactor containing both; a first transaminase enzyme and a second transaminase enzyme to produce (i) the desired alpha-amino acid, $AA_d$ and (ii) a third alpha-keto acid, $KA_{prod}$;
   (b) removing $KA_{prod}$ from the other keto acids, amino acids and enzymes wherein $AA_d$ and $KA_{pre}$, $AA_t$ and $KA_t$, and $AA_{NH2}$ and $KA_{prod}$ are interconvertible, respectively, by amino group transfer; and,
   (c) recovering $AA_d$ from the other amino acids, keto acids and enzymes;

and wherein said first transaminase efficiently catalyzes reaction (i) but not reaction (ii) and said second transaminase efficiently catalyzes reaction (ii) but not reaction (i):

$$AA_{NH2} + KA_f \rightleftharpoons AA_t + KA_{prod}$$

$$AA_t + KA_{pre} \rightleftharpoons AA_d + KA_f.$$

2. The process of claim 1, wherein $KA_{prod}$ is removed from the other keto acids, amino acids and enzymes by decarbozylation of $KA_{prod}$.

3. The process of claim 2, wherein the decarboxylation is accomplished using an enzyme which effectively catalyzes the decarboxylation of $KA_{prod}$ but not of $KA_{pre}$ or $KA_t$.

4. The process of claim 1, wherein $KA_{prod}$ is removed from the other keto acids, amino acids and enzymes by reductive amination of $KA_{prod}$ to produce $AA_{NH2}$.

5. The process of claim 4, wherein the reductive amination of $KA_{prod}$ is accomplished enzymatically in the presence of an appropriate enzyme preparation and a nitrogen source.

6. The process of claim 1, 3 or 5 wherein the enzymes are purified or partially purified enzyme preparations, or are contained in whole cells.

7. The process of claim 6, wherein each enzyme is immobilized on an insoluble support.

8. The process of claim 7 wherein said immobilization support is controlled pore ceramic particle or controlled pore glass particle.

9. The process of claim 8 wherein the enzymes are immobilized on a polyethyleneimine treated particle.

* * * * *